United States Patent [19]

Farber

[11] 4,035,393

[45] July 12, 1977

[54] CHROMOGENIC DERIVATIVES OF BIS-1,1-DISUBSTITUTED ETHYLENE AND A PROCESS FOR PREPARING THEM

[75] Inventor: Sheldon Farber, Appleton, Wis.

[73] Assignee: NCR Corporation, Dayton, Ohio

[21] Appl. No.: 566,847

[22] Filed: Apr. 10, 1975

[51] Int. Cl.² ............... C07D 407/04; C07D 403/04
[52] U.S. Cl. .................... 260/343.3 R; 260/295 F; 260/343.2 R
[58] Field of Search ............ 260/343.3 R, 343.2 R, 260/295 F

[56] References Cited

U.S. PATENT DOCUMENTS 3,766,214  10/1973  Lin et al. ................... 260/343.3

OTHER PUBLICATIONS

Elderfield, Heterocyclic Compounds, vol. 2, p. 296 (1951).

Primary Examiner—Robert Gerstl
Attorney, Agent, or Firm—E. Frank McKinney

[57] ABSTRACT

A process for preparing a chromogenic compound of normally colorless form is disclosed; — the chromogenic compound having the following structural formula:

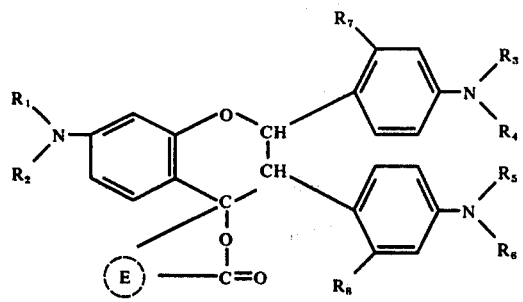

R can be, among several others, hydrogen, alkyl, alkoxy, aryl, and heterocyclic, substituted and unsubstituted; and E can be a broad family of aromatic and heterocyclic structures. The compound is eligible for use in pressure-sensitive record materials and manifold marking systems.

6 Claims, 1 Drawing Figure (I) 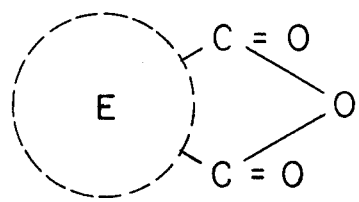
(A) 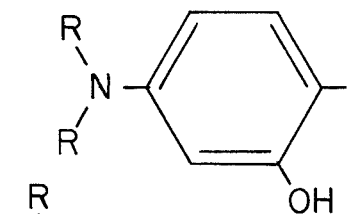
(II) 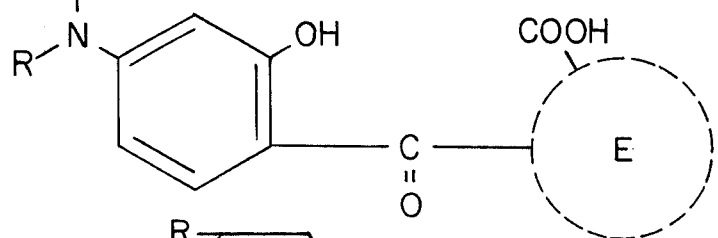
(B) 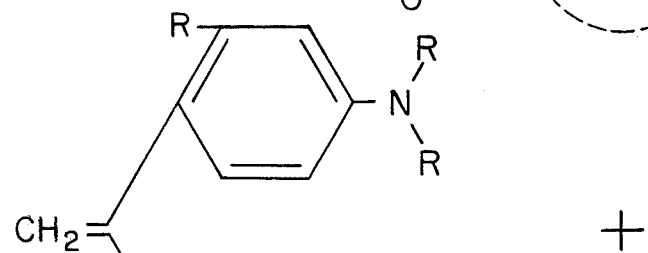 +
(III) 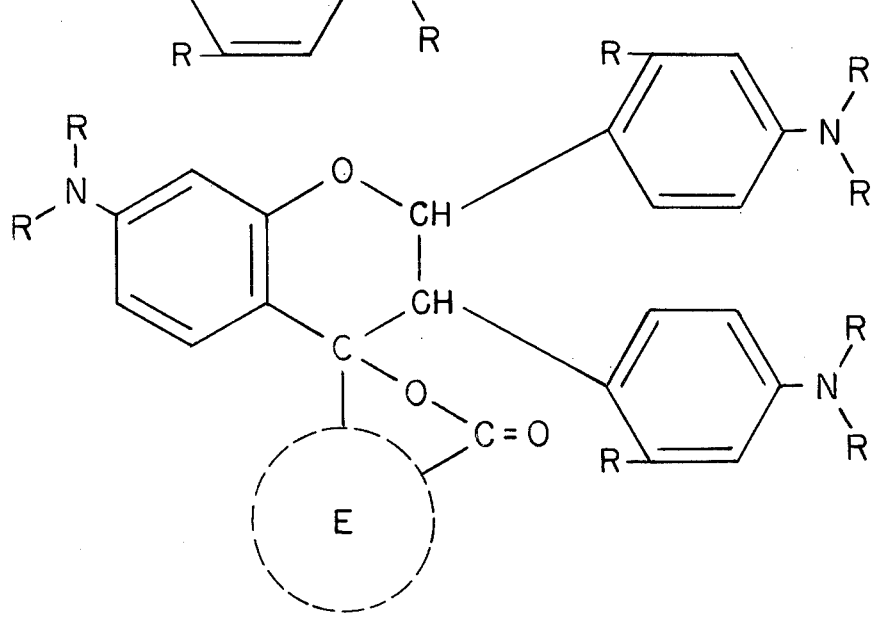

CHROMOGENIC DERIVATIVES OF BIS-1,1-DISUBSTITUTED ETHYLENE AND A PROCESS FOR PREPARING THEM

BACKGROUND OF THE INVENTION

1. Field of the Invention

This invention pertains to a process for preparing colorable chromogenic compounds eligible for use in pressure-sensitive record material and to the compounds themselves. Pressure-sensitive mark-forming record systems, single sheet and manifold, are improved by use of these compounds.

More specifically, this invention relates to chromogenic compounds which have the form of substantially colorless or slightly colored solids, or which approach being colorless when in liquid solution; but, which may be converted to dark-colored forms upon reactive contact with acidic material. As used in mark-forming systems, marking in desired areas on support webs or sheets may be accomplished by effecting localized reactive contact between the chromogenic material and the acidic material on or in such web or sheet, such material being brought thereto by transfer, or originally there, in situ. The desired reactive contact forms dark-colored materials in the intended image-marking areas.

The chromogenic compounds of this invention have the following general structure:

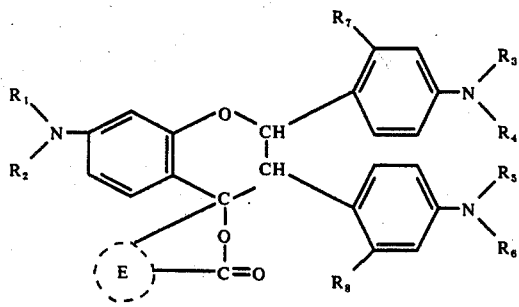

R can be, among several others, hydrogen, alkyl, cycloalkyl, halo, alkoxy, and aryl, substituted or unsubstituted; and E is a broad family of aromatic structures.

2. Description of the Prior Art

Several phthalide and fluoran chromogenic compounds and processes for preparing them have been disclosed. For example, U.S. Pat. No. 3,491,111, issued Jan. 20, 1970, discloses indol- and carbazol-substituted phthalides. U.S. Pat. No. 2,417,897, issued Mar. 25, 1947, discloses crystal violet lactone. U.S. Pat. No. 3,681,390, issued Aug. 1, 1972, discloses aryl-substituted fluorans.

U.S. Pat. No. 3,672,935, issued June 27, 1972, discloses use of colorless chromogenic compounds in pressure-sensitive record material.

G. Hallas, in the Journal of the Society of Dyers and Colourists, in September, 1967 at pages 368 to 373 and in June, 1970 at pages 237–242, discusses the effects of extended conjugation on colored dye compounds.

SUMMARY OF THE INVENTION

Colorable chromogenic compounds, above disclosed, have been discovered which compounds are initially substantially colorless but produce dark-colored products on reaction with certain acid materials. It is an object of this invention to provide such compounds and methods for making them.

An important use for the compounds of this invention resides in their incorporation into pressure-sensitive record systems as a colorable reactant for development of color on application of a mark-forming force. Hence, it is an object of this invention to provide substances and a process for making such substances having color reactant response and chromogenic properties, which substances can be incorporated in a web or coated onto the surface of a web to provide a record sheet or a manifolding unit, and which are useful in carrying out methods of marking involving reactive contact with a color-activating material to develop dark-colored materials in areas where marking is desired.

It is an object of this invention to provide modified compounds and a process for making the modified compounds, which are substantially colorless, or slightly colored, offering a variety of chromogenic characteristics.

BRIEF DESCRIPTION OF THE DRAWING

The chromogenic compounds of this invention include a large variety of several moieties with benzopyran structure and lactone rings being necessarily common to all compounds. In order to more completely and more distinctly disclose the variety of moiety combinations which forms a part of this invention, a drawing is included which is a schematic representation of the combinations, by structural formula.

The drawing presents a step-by-step structural development of the compounds of this invention, as they can be prepared. A dicarboxylic anhydride (I) is combined with a substrate reactant (A) to yield a keto acid (II) which is, in turn, combined with a vinyl-containing substrate reactant (B) to yield the chromogenic compound (III) of this invention.

The dicarboxylic anhydride (I), in the drawing, includes E as the supporting molecular structure. E represents a large variety of structures including aromatic and heterocyclic, substituted and unsubstituted. The substitutions include halo, nitro, cyano, and alkylthio, alkoxy, alkyl and dialkylamino with alkyl of less than seven carbon atoms. Halogen or halo-, in this invention, means fluorine, chlorine, bromine and iodine.

(A) is a phenyl moiety substituted para by an amino and substituted ortho by a hydroxy. The (A) is combined with (I) to yield a phenolic benzophenone keto acid (II). The keto acid is condensed with an ethylene compound (B) to yield the chromogenic compound of this invention (III).

(I) is not required to be a dicarboxylic anhydride. A dicarboxylic acid will suffice if the keto acid-forming reaction is conducted under dehydrating conditions such as in acetic anhydride. Moreover, the ethylene compound (B) can be a methyl carbinol under dehydrating conditions wherein the methyl carbinol is equivalent to, and reacts as, an ethylene compound.

DETAILED DESCRIPTION OF THE INVENTION

What is considered to be the invention is the product of reaction between a phenolic benzophenone keto acid and an ethylene compound to yield a colorless but colorable chromogenic material. The process for making the chromogenic material is also considered to be the invention, wherein an ethylene compound, or its equivalent, is reacted with phenolic benzophenone keto acid. At the present time, the chromogenic compounds of this invention enjoy extensive eligibility for use in pressure-sensitive and thermally-sensitive mark-forming systems.

Pressure-sensitive mark-forming systems provide a marking system of disposing on and/or within sheet support material unreacted mark-forming components and a liquid solvent in which each of the mark-forming components is soluble, said liquid solvent being present in such form that it is maintained isolated by a pressure-rupturable barrier from at least one of the mark-forming components until application of pressure causes a breach of the barrier in the area delineated by the pressure pattern. The mark-forming components are thereby brought into reactive contact, producing a distinctive mark.

The method of marking comprises providing a chromogenic compound selected from among the above-mentioned compounds and bringing such chromogenic compound into reactive contact, in areas where marking is desired, with an acidic color-activating substance to produce a dark-colored form of the chromogenic compound.

The acidic materials can be any compound within the definition of a Lewis acid, i.e., an electron acceptor. Preferably, acidic organic polymers such as phenolic polymers are employed as the acidic material. It is noted that the polymeric mark-forming components should have a common solubility with the chromogenic compound in at least one liquid solvent when the acid-reacting material is a phenolic or other organic acidic polymer. It is also noted that in a single system several chromogenic compounds can be used with the same or different polymeric materials. Several polymeric materials can be reactively contacted with a single chromogenic compound or with a mixture of chromogenic compounds.

The acidic polymeric material useful in this invention includes phenol polymers, phenol acetylene polymers, alkyl-phenol-acetylene polymers, maleic acid-rosin resins, partially or wholly hydrolyzed styrene-maleic anhydride copolymers and ethylene-maleic anhydride copolymers, carboxy polymethylene and wholly or partially hydrolyzed vinyl methyl ether maleic anhydride copolymers and mixtures thereof.

When the acidic material is one of the aforementioned organic polymers, the liquid solvent chosen must be capable of dissolving the mark-forming components. The solvent can be volatile or non-volatile, and a single or multiple component solvent may be used which is wholly or partially volatile. Examples of volatile solvents useful in the afore-described basic chromogen-acidic polymer are toluene, petroleum distillate, perchloroethylene, and xylene. Examples of non-volatile solvents are high-boiling point petroleum fractions, dioctyl adipate, biphenyls, diphenyl alkanes, and the like.

Generally, the solvent chosen should be capable of dissolving at least 0.3 percent, by weight, of the chromogenic compounds and at least about 3—5 percent, by weight, of the polymeric material. A further criterion of the solvent is that it must not interfere with the mark-forming reaction.

The support member on which the components of the system are disposed may comprise a single or dual sheet assembly. In the case where all components are disposed on a single sheet surface, the record material is referred to as a "self-contained" system. Where there must be a migration of the solvent, with or without mark-forming component, from one sheet to another, the record material is referred to as a "transfer" system. (Such a system can also be referred to as a "two-fold" system, in that at least two sheets are required and each sheet includes a component, or components, essential to the mark-forming reaction.) Where a copious amount of the colored reaction product in liquid form is produced on a surface of one sheet, it can produce a mark by transfer to a second sheet as a colored mark.

The polymeric material can be dissolved in ink composition vehicles to form a printing "ink" of colorless character and, thus, can be used to spot-print a proposed record sheet unit sensitized for recording in a reaction-produced color in those areas by application of a solution of the chromogenic material. In the case of phenolic polymer, a printing ink can be made of up to 75% by weight, of the phenolic polymeric material in a petroleum solvent to a viscosity suitable for printing purposes.

In the mark-forming system herein, the acidic mark-forming component(s) reacts with the chromogenic material(s) to effect distinctive color formation or color change. In a multi-sheet system in which an acid organic polymer is employed, it is desirable to include other materials to supplement the reactants. For example, kaolin can be added to improve the transfer of the liquid and/or the dissolved materials between the sheets. In addition, other materials such as bentonite, attapulgite, talc, feldspar, halloysite, magnesium trisilicate, silica gel, pyrophyllite, zinc sulfide, calcium sulfate, calcium citrate, calcium phosphate, calcium fluoride, barium sulfate and tannic acid can be included. It should be noted that mineral materials such as kaolin, attapulgite, silica gel, silton clay, and the like can, also, be used alone or in combination with other materials as an acidic material coreactant.

Various methods known to the prior art and disclosd in the aforementioned U.S. Pat. No. 3,672,935 can be employed in coating compositions of the mark-forming materials into their supporting sheets. An example of the compositions which can be coated onto the surface of an underlying sheet of a two-sheet system to react with the chromogenic material on the underside of any overlying sheet is as follows:

| Coating Composition | Percent by Weight |
| --- | --- |
| Phenolic polymer mixture | 17 |
| Paper coating kaolin (white) | 57 |
| Calcium carbonate | 12 |
| Styrene butadiene latex | 4 |
| Ethylated starch | 8 |
| Gum arabic | 2 |
| | 100 |

Thermally-sensitive mark-forming systems can also be prepared using the compounds of this invention.

The compounds of this invention are prepared as will be discussed in the examples which follow. Referring, again, to the drawing;— in (I), E can be the following:

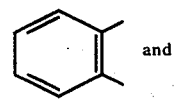 and 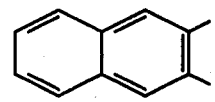

unsubstituted and alkyl-, chloro-, dichloro-, trichloro-, tetrachloro-, bromo-, dibromo-, tribromo-, tetrabromo-, nitro-, and dialkylamino-substituted;

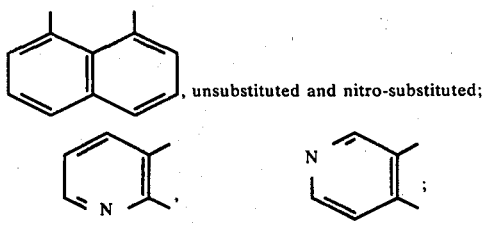, unsubstituted and nitro-substituted;

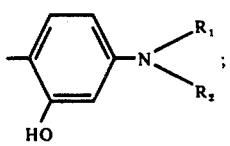

(A) is 2-hydroxy-4-disubstituted amino phenyl represented by the structure:

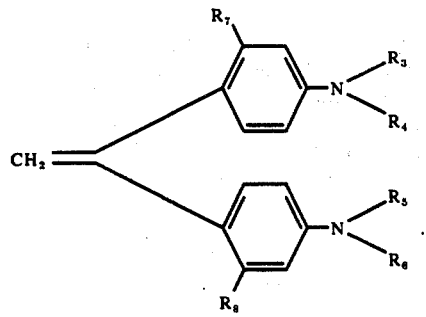

(B) is bis-1,1-(2-substituted-4-disubstituted amino) ethylene represented by the structure:

$R_1$, $R_2$, $R_3$, $R_4$, $R_5$ and $R_6$ are hydrogen, alkyl, substituted phenyl, unsubstituted phenyl, benzyl, acyl, and cycloalkyl; and $R_7$ and $R_8$ are hydrogen, alkyl, alkoxy, halo, dialkylamino, monoalkylamino, amino and acylamino. Both of $R_1$ and $R_2$ or $R_3$ and $R_4$ or $R_5$ and $R_6$ are not phenyl.

It should be understood that "alkyl" and any group requiring alkyl, such as "alkoxy" means methyl, ethyl, propyl (including isopropyl), butyl (including isobutyl and tert-butyl), pentyl (including all five-carbon isomers), hexyl (includng all six-carbon isomers), and the like having less than seven carbon atoms.

This invention is further illustrated by the following examples. The reactants and the proportions and other specific conditions are represented as being typical and should not be considered to limit the invention.

DESCRIPTION OF PREFERRED EMBODIMENTS

EXAMPLE

Preparation of spiro [2,3-dihydro-2,3-bis-p-dimethyl-aminopheyl)-7-(N-p-toluidino)]4,7'—2°H-benzofur-2-one.

With reference to the drawing in respect of this example and like examples which follow, the description of compound preparation commences at (II), the keto-acid, because preparation of the keto-acid is known or not difficult. For instance, one keto-acid of this example is easily prepared by mol-for-mol combination of phthalic anhydride (I) and m-(N-p-tolyl)aminophenol (A) in the presence of a catalyst such as aluminum chloride or other Friedel-Crafts catalyst and a solvent such as methylene chloride. The phthalic anhydride can be substituted or not as previously described; and the m-(N-p-tolyl)aminophenol can be any amino-substituted hydroxyphenyl moiety, as previously described. Any generally recognized Friedel-Crafts catalyst is eligible and suitable solvents such as carbontetrachloride, chlorobenzene, dichlorobenzene, and nitrobenzene are eligible.

For ease in understanding, the examples are summarized in listings of components, the (A) components are listed as radicals, and the (B) components are listed as compounds. Such listing is believed to facilitate comprehension of the molecular structures.

Combining an appropriate keto-acid, for example 2'-carboxy-2-hydroxy-4-toluidino benzophenone (II), with an appropriate ethylene base, results in a compound of this invention. This example will be given with details of an eligible system of reaction conditions and will be followed by an additional listing of exemplary compounds. A solution of 17.3 grams of the keto-acid (moiety II from I and A), 16.0 grams of bis-1,1-(p-dimethylaminophenyl)ethylene (moiety (B) wherein the amino-R is methyl), and 200 milliliters of acetic anhydride is refluxed for a few minutes and poured into ice and ammonia. The system is extracted with toluene, dried in the toluene using sodium sulfate, and the toluene is evaporated. The residue is dissolved in toluene and chromatographed on alumina. The product is glassy and exhibits a melting range of 90–155° centigrade. A solution of the product imparts a green color to paper coated with a phenolic resin or silton clay or a combination of the two. A reflectance spectrum of the green color has absorption peaks at about 660 nanometers.

This example is also conducted using 4-dimethylamino-phthalic anhydride, 4-di-t-butylaminophthalic anhydride, 3-methylphthalic anhydride, 3-butyl-5-ethylphthalic anhydride, 4-nitrophthalic anhydride, equivalently substituted 1,8- and 2,3-naphthalene dicarboxylic acid anhydride compounds and 2,3- and 3,4- pyridinedicarboxylic acid anhydrides.

This example is also conducted using bis-1,1-(-di-t-butylaminophenyl)ethylene, bis-1,1-(2-ethoxy-4-dimethylaminophenyl) ethylene, or bis-1,1-(2-methyl-4-diethylaminophenyl)ethylene. It should be pointed out that many of the ethylene compounds, themselves, are chromogenic compounds.

Lower aliphatic straight-chain anhydrides (having less than five carbon atoms) are eligible for use in place of the acetic anhydride. Preferred are propionic anhydride, iso-butyric anhydride and butyric anhydride.

Example, Summarized.

(I) phthalic anhydride (A) 2-hydroxy-4-dimethylaminophenyl
(B) bis-1,1-(p-dimethylaminophenyl)ethylene
green.
also (B) bis-1,1-(p-di-t-butylaminophenyl)ethylene
also (B) bis-1,1-(2-ethoxy-4-dimethylaminophenyl)ethylene
also (B) bis-1,1-(p-benzylaminophenyl)ethylene
also (A) 2-hydroxy-4-diethylaminophenyl
(A) 2-hydroxy-4-(p-methylphenyl)aminophenyl
(B) bis-1,1-(p-dimethylaminophenyl)ethylene green.
  also (B) bis-1,1-(2-pentyl-4-dimethylaminophenyl)ethylene
  also (B) bis-1,1-(p-phenylaminophenyl)ethylene
also (A) 2-hydroxy-4-(p-hexylphenyl)aminophenyl
(A) 2-hydroxy-4-benzylaminophenyl
  (B) bis-1,1-(p-dimethylaminophenyl)ethylene green.
  also (B) bis-1,1-(2-chloro-4-diethylaminophenyl)ethylene
  also (B) bis-1,1-(2-dibutylamino-4-dimethylaminophenyl)ethylene
  also (B) bis-1,1-(2-methylamino-4-dimethylaminophenyl)ethylene
  also (B) bis-1,1-(2-amino-4-dimethylaminophenyl)ethylene
  also (B) bis-1,1-(2-acetamino-4-dimethylaminophenyl)ethylene
also (A) 2-hydroxy-4-hexylaminophenyl
(A) 2-hydroxy-4-cyclohexylaminophenyl
  (B) bis-1,1-(p-dimethylaminophenyl)ethylene green.
  also (B) bis-1,1-(2-bromo-4-dimethylaminophenyl)ethylene
also (I) 3,4,5,6-tetrabromophthalic anhydride and tribromo, dibromo and bromo
(I) 3,4,5,6-tetrachlorophthalic anhydirde and trichloro, dichloro and chloro
(A) 2-hydroxy-4-diethylaminophenyl
  (B) bis-1,1-(p-dimethylaminophenyl)ethylene green
  also (B) bis-1,1-(2-butylamino-4-diethylaminophenyl)ethylene

What is claimed is:

1. A compound represented by the formula:

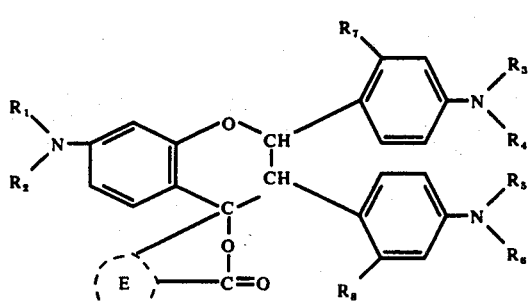

wherein
E is:

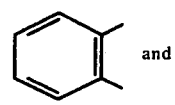 and 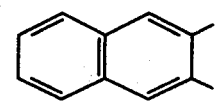, unsubstituted and alkyl-, chloro-, dichloro-, trichloro-, tetrachloro-, bromo-, dibromo-, tribromo-, tetrabromo-, nitro-, and dialkylamino-substituted,

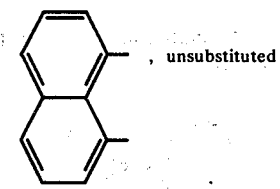, unsubstituted and nitro-substituted; 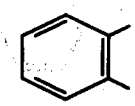;

$R_1$, $R_2$, $R_3$, $R_4$, $R_5$, and $R_6$ are: hydrogen, alkyl, phenyl, benzyl, and cyclohexyl, but both of $R_1$ and $R_2$ or $R_3$ and $R_4$ or $R_5$ and $R_6$ are not phenyl;
$R_7$ and $R_8$ are: hydrogen, alkyl, alkoxy, halo, dialkylamino, monoalkylamino and amino and
each alkyl has less than seven carbon atoms.

2. The compound of claim 1 wherein E is

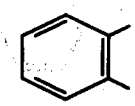, unsubstituted.

3. The compound of claim 2 wherein $R_1$ and $R_2$ are alkyl having less than seven carbon atoms.
4. The compound of claim 2 wherein $R_1$ is phenyl.
5. The compound of claim 2 wherein $R_1$ is benzyl.
6. The compound of claim 2 wherein $R_1$ is cyclohexyl.

* * * * *